US00PP11917P2

(12) United States Plant Patent
VandenBerg

(10) Patent No.: US PP11,917 P2
(45) Date of Patent: Jun. 12, 2001

(54) CHRYSANTHEMUM PLANT NAMED 'YOEUGENE'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/270,786

(22) Filed: Mar. 17, 1999

(51) Int. Cl.[7] ..... A01H 5/00
(52) U.S. Cl. ..... Plt./286

(58) Field of Search ..... Plt./286, 297

*Primary Examiner*—Howard J. Locker
(74) *Attorney, Agent, or Firm*—C. A. Whealy

(57) ABSTRACT

A distinct cultivar of Chrysanthemum plant named 'Yoeugene', characterized by its upright, outwardly spreading and uniformly mounded plant habit; freely branching habit; uniform and early flowering; numerous daisy-type inflorescences that are about 7.5 cm in diameter; initially yellow then bright pink-colored ray florets; slow maturing disc florets; and good postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yoeugene.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in October, 1994, in Salinas, Calif., of a proprietary Chrysanthemum seedling selection identified as code number YB-6364 as the female, or seed, parent, with the commercial Chrysanthemum cultivar Miramar, disclosed in U.S. Plant Pat. No. 7,469, as the male, or pollen, parent.

The new Chrysanthemum was discovered and selected by the Inventor as a flowering plant within the progeny of the stated cross in a controlled environment in Fort Myers, Fla., in November, 1995. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yoeugene has not been observed under all possible environmental conditions. The phenotype may vary somewhat with variations in environment such as temperature, daylength and light intensity, without, however, and variance in genotype.

The following traits have been repeatedly observed and are determined to be the unique characteristics of 'Yoeugene'. These characteristics in combination distinguish 'Yoeugene' as a new and distinct Chrysanthemum:

1. Upright, outwardly spreading and uniformly mounded plant habit.

2. Freely branching habit, very full and dense plants.

3. Uniform and early flowering.

4. Floriferous, numerous daisy-type inflorescences that are about 7.5 cm in diameter.

5. Initially yellow then bright pink-colored ray florets.

6. Slow maturing disc florets.

7. Good postproduction longevity with inflorescences and leaves maintaining good substance and color for about three or four weeks in an interior environment.

The new Chrysanthemum can be compared to the Chrysanthemum cultivar Regal Davis, disclosed in U.S. Plant Pat. No. 8,292. However in side-by-side comparisons in Salinas, Calif., and Leamington, Ontario, Canada, under commercial practice, plants of the new Chrysanthemum differ from plants of the cultivar Regal Davis in the following characteristics:

1. Plants of the new Chrysanthemum are larger and more vigorous than plants of the cultivar Regal Davis.

2. Leaves of the new Chrysanthemum are larger and less likely to fleck than leaves of the cultivar Regal Davis. In addition, plants of the new Chrysanthemum have better foliage retention than plants of the cultivar Regal Davis.

3. Plants of the new Chrysanthemum flower about four or five days earlier than plants of the cultivar Regal Davis.

4. Inflorescences of the new Chrysanthemum are larger than inflorescences of the cultivar Regal Davis.

5. Ray florets of the new Chrysanthemum are initially yellow whereas ray florets of the cultivar Regal Davis are initially pink. Mature ray florets of the new Chrysanthemum are lighter pink than ray florets of the cultivar Regal Davis.

6. Ray florets of the new Chrysanthemum are convex in cross-section whereas ray florets of the cultivar Regal Davis are flat to concave.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yoeugene', The photograph at the bottom of the first sheet comprises a close-up view of upper (left) and lower (right) surfaces of typical inflorescences and upper (left) and lower (right) surfaces of typical leaves of the cultivar Yoeugene.

The photograph at the top of the second sheet comprises a side perspective view of typical flowering plants of 'Yoeugene' (left) and 'Regal Davis' (right).

The photograph at the bottom of the second sheet comprises a close-up view of upper surfaces of typical inflorescences and leaves of plants of 'Yoeugene' (left) and 'Regal Davis' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yoeugene.

Commercial classification: Daisy spray-type pot Chrysanthemum.

Parentage:

*Female or seed parent*.—Proprietary *Dendranthema grandiflora* seedling selection identified as code number YB-6364.

*Male or pollen parent*.—*Dendranthema grandiflora* cultivar Miramar, disclosed in U.S. Plant Pat. No. 7,469.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Herbaceous daisy pot Chrysanthemum typically grown as a spray-type. Inverted triangle; stems upright and outwardly spreading giving a uniformly mounded appearance to the plant. Freely branching; about five lateral branches develop after removal of terminal apex (pinching); dense and full plants.

*Plant height*.—About 31 cm.

*Plant width*.—About 42 cm.

*Stem color*.—Close to 141A.

*Stem texture*.—Pubescent.

*Foliage description*.—Arrangement: Alternate. Length: About 7.9 cm. Width: About 4.8 cm. Apex: Cuspidate to mucronate. Base: Attenuate. Margin: Palmately lobed, sinuses between lateral lobes mostly parallel to divergent. Texture: Upper and lower surfaces with very fine pubescence; veins prominent on lower surface. Petiole length: About 2.4 cm. Color: Young foliage upper surface: 147A. Young foliage lower surface: Close to 147B. Mature foliage upper surface: 147A. Mature foliage lower surface: 147B. Venation upper surface: Close to 147A. Venation lower surface: Close to 147B.

Inflorescence description:

*Appearance*.—Daisy inflorescence form with oblong-shaped ray florets. Inflorescences borne on terminals above foliage, arising from leaf axils. Disk and ray florets arranged acropetally on a capitulum.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 8 to 8.5 weeks later.

*Postproduction longevity*.—Inflorescences and leaves will maintain good color and substance for about three or four weeks in an interior environment.

*Quantity of Inflorescences*.—Very floriferous; about eight or nine inflorescences per lateral branch or about 40 to 45 inflorescences per plant.

*Inflorescence bud*.—Height: About 7 mm. Diameter: About 9 mm. Color: Close to 147A.

*Inflorescence size*.—Diameter: About 7.5 cm. Depth (height): About 1.7 cm. Diameter of disc: About 1.7 cm.

*Ray florets*.—Shape: Oblong with short corolla tube. Orientation: Mostly flat, but twisted; slightly upright; somewhat convex. Length: About 3.5 cm. Width: About 1.1 cm. Apex: Cuspidate/emarginate. Margin: Entire. Texture: Smooth, glabrous, satiny. Number of ray florets per inflorescence: About 22. Color: When opening: Yellow, 5A. Fully opened, upper surface: Pink, 59D fading to 70B. Fully opened, lower surface: 4C to 4D to white.

*Disc florets*.—Shape: Tubular. Apex: Serrated. Length: About 6 mm. Width: Apex: About 2 mm. Base: About 1 mm. Number of disc florets per inflorescence: About 177. Color: Immature: Initially green, 144A, then more yellow than 154A; slow maturing. Mature: Apex: 9A. Base: White, 155D.

*Peduncles*.—Aspect: Angled about 45° to stem. Strength: Strong, but flexible. Length: First peduncle: About 4.9 cm. Fourth peduncle: About 8.1 cm. Texture: Pubescent. Color: Close to 141A.

*Reproductive organs*.—Androecium: Present on disc florets only. Anther color: 12A to 13A. Pollen: Amount: Moderate. Color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yoeugene', as illustrated and described.

* * * * *

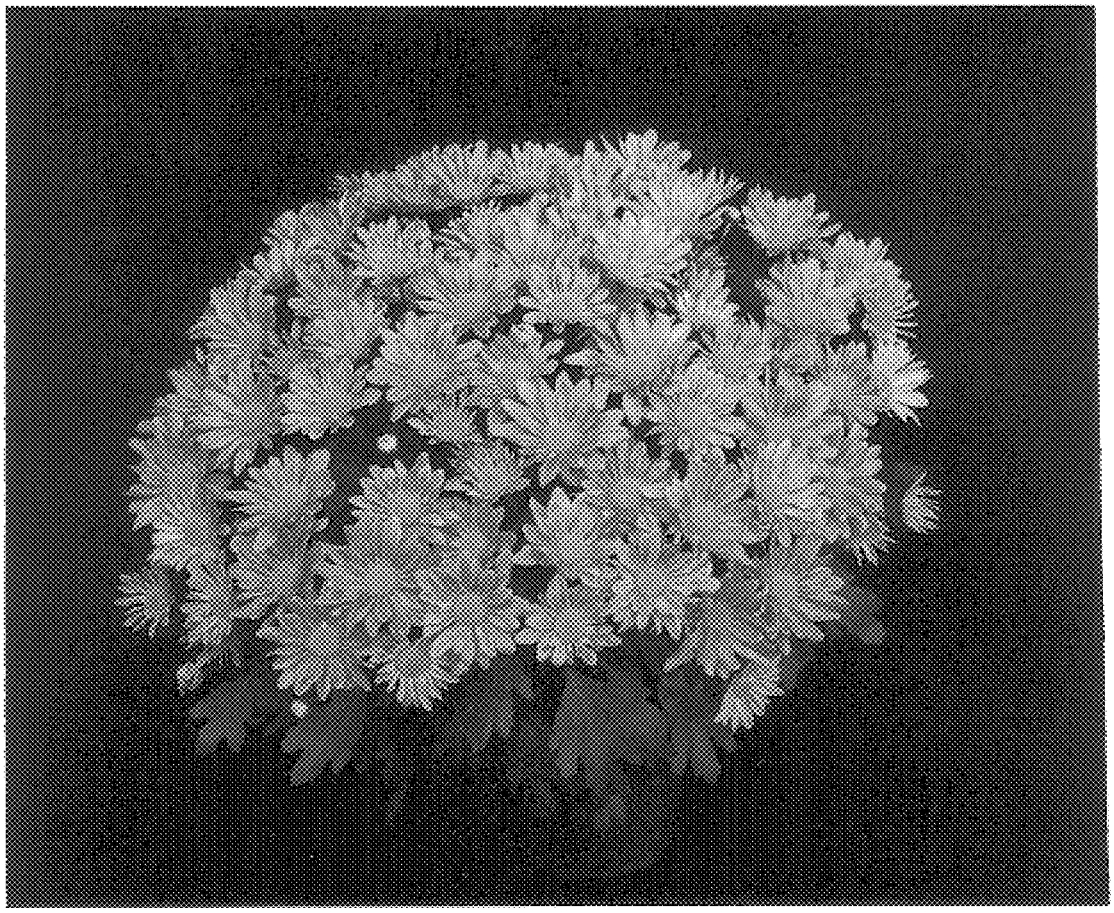
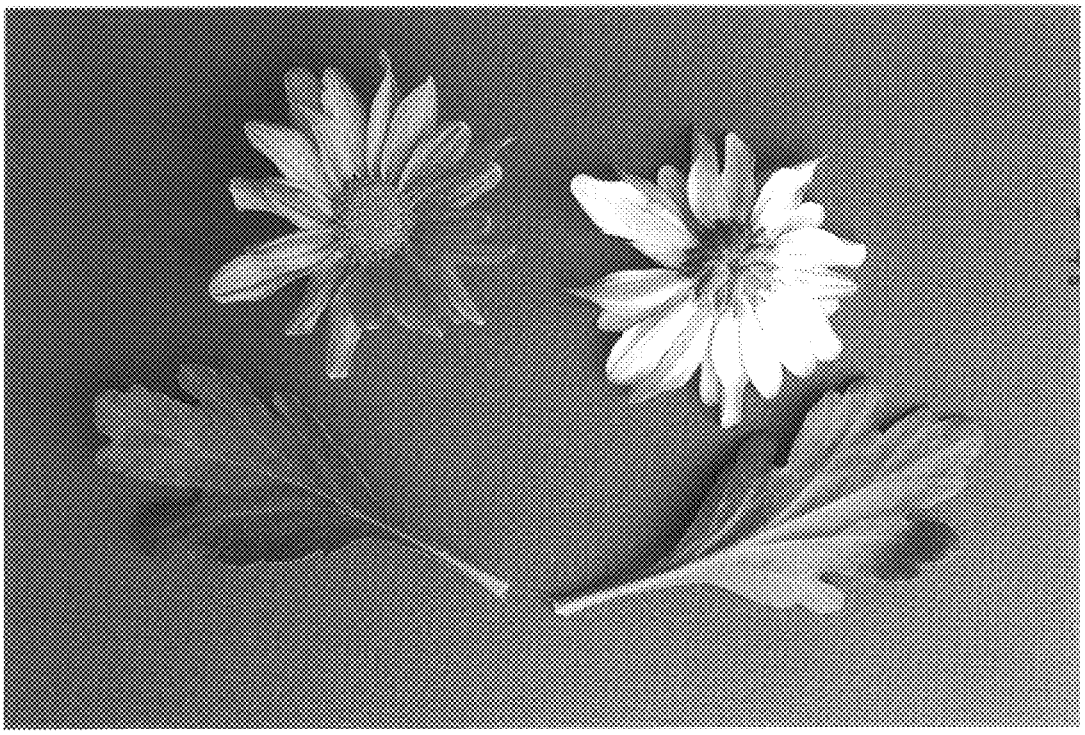

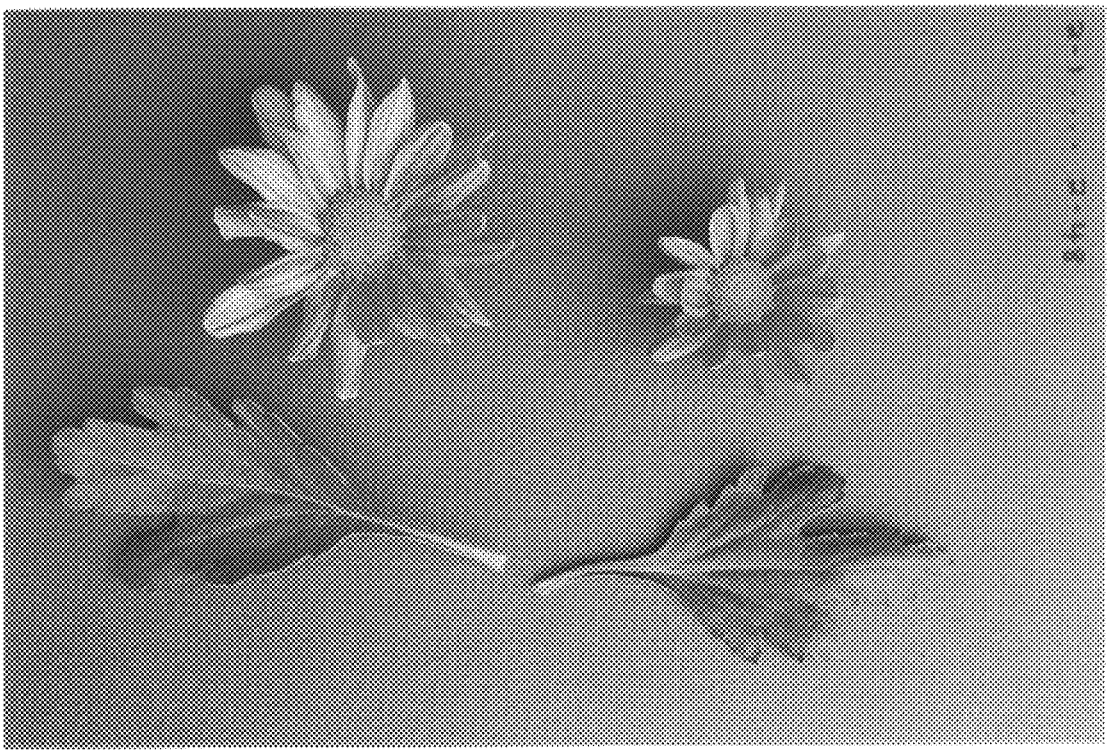

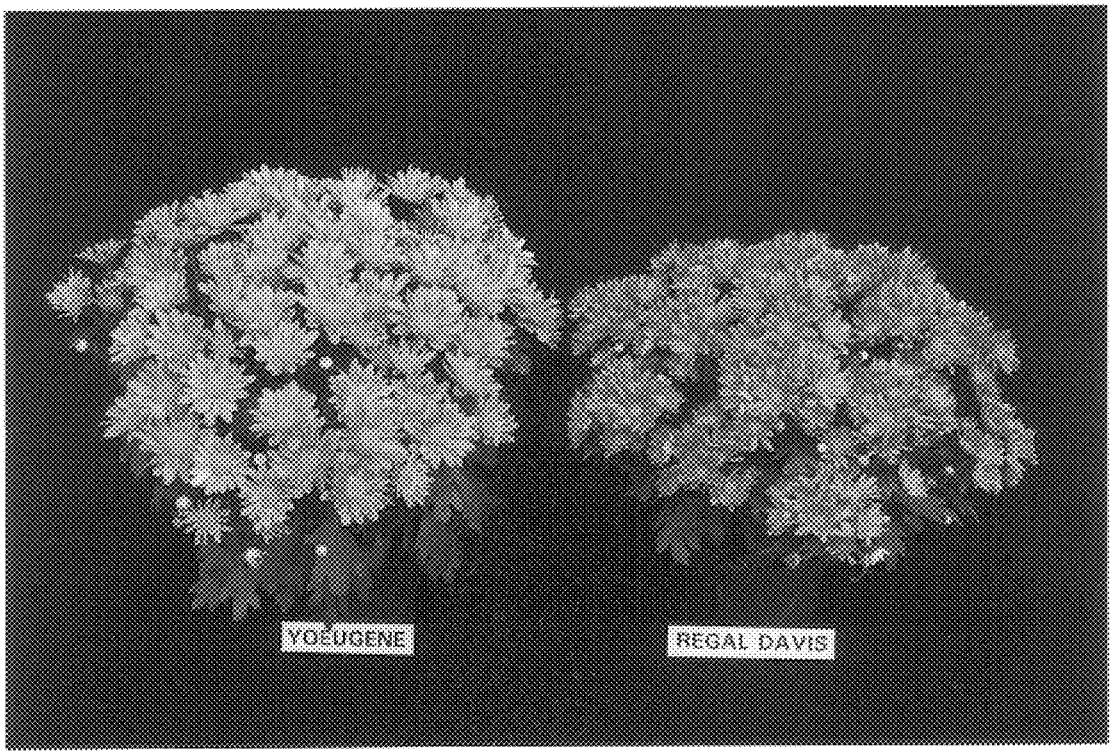
YOEUGENE
REGAL DAVIS